(12) United States Patent
Wang et al.

(10) Patent No.: US 9,151,881 B2
(45) Date of Patent: Oct. 6, 2015

(54) PHASE GRATING FOR MASK INSPECTION SYSTEM

(71) Applicant: KLA-Tencor Corporation, Milpitas, CA (US)

(72) Inventors: Daimian Wang, Fremont, CA (US); Oleg Khodykin, San Jose, CA (US); Daniel Wack, Fredericksburg, VA (US); Li Wang, San Ramon, CA (US); Yanwei Liu, Danville, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/786,049

(22) Filed: Mar. 5, 2013

(65) Prior Publication Data

US 2014/0131586 A1 May 15, 2014

Related U.S. Application Data

(60) Provisional application No. 61/725,223, filed on Nov. 12, 2012.

(51) Int. Cl.
| | |
|---|---|
| *G01J 1/42* | (2006.01) |
| *G02B 5/18* | (2006.01) |
| *G01J 3/18* | (2006.01) |
| *G01N 21/956* | (2006.01) |
| *G03F 1/00* | (2012.01) |
| *G02B 5/20* | (2006.01) |

(52) U.S. Cl.
CPC .................. *G02B 5/1838* (2013.01); *G01J 3/18* (2013.01); *G01N 21/956* (2013.01); *G02B 5/203* (2013.01); *G03F 1/0092* (2013.01); *G01N 2021/95676* (2013.01)

(58) Field of Classification Search
CPC .................. G01N 2021/95676; G01N 21/956; G02B 2006/12107; G02B 6/02061; G02B 6/34; G02B 5/1838; G02B 5/203; G02F 2201/305; G01J 3/18
USPC .......................................................... 250/372
See application file for complete search history.

(56) References Cited

U.S. PATENT DOCUMENTS

| | | | | |
|---|---|---|---|---|
| 6,392,792 | B1 * | 5/2002 | Naulleau ........................ | 359/360 |
| 6,678,037 | B2 * | 1/2004 | Van Elp et al. ................. | 355/67 |
| 6,713,753 | B1 * | 3/2004 | Rovira et al. .................. | 250/225 |
| 7,061,615 | B1 * | 6/2006 | Lowe-Webb ................. | 356/401 |
| 7,084,412 | B2 | 8/2006 | Weiss | |
| 7,230,705 | B1 * | 6/2007 | Yang et al. .................... | 356/401 |

(Continued)

FOREIGN PATENT DOCUMENTS

JP     2009-053006 A     3/2009

OTHER PUBLICATIONS

PCT Search Report for PCT/US2013/069278, Mail date Feb. 26, 2014, 3 pages.

*Primary Examiner* — David J Makiya
*Assistant Examiner* — Taeho Jo
(74) *Attorney, Agent, or Firm* — Suiter Swantz pc llo

(57) ABSTRACT

Spectral Purity Filters, or SPFs, are disclosed. Such SPFs are designed to block out the 1030 nm drive laser and other undesired out of band light in a EUV mask inspection system. Different phase grating configurations for near normal incidence and grazing incidence are provided in the present disclosure and are configured specifically for EUV mask inspection.

37 Claims, 9 Drawing Sheets

(56) References Cited

U.S. PATENT DOCUMENTS

| | | | |
|---|---|---|---|
| 7,236,244 B1* | 6/2007 | Yang et al. | 356/400 |
| 7,248,667 B2 | 7/2007 | Weiss et al. | |
| 7,250,620 B2* | 7/2007 | Wurm et al. | 250/504 R |
| 7,319,509 B2 | 1/2008 | Singer | |
| 7,453,645 B2 | 11/2008 | Klunder et al. | |
| 8,198,613 B2 | 6/2012 | Moriya et al. | |
| 8,459,807 B2* | 6/2013 | Herbert et al. | 359/530 |
| 2003/0002622 A1 | 1/2003 | Martynov et al. | |
| 2005/0024614 A1* | 2/2005 | Bakker | 355/67 |
| 2005/0112510 A1* | 5/2005 | Bakker | 430/396 |
| 2005/0206869 A1* | 9/2005 | Voorma et al. | 355/67 |
| 2006/0245057 A1 | 11/2006 | Van Herpen et al. | |
| 2010/0039707 A1* | 2/2010 | Akahane et al. | 359/576 |
| 2010/0182666 A1* | 7/2010 | Herbert et al. | 359/200.7 |
| 2010/0284064 A1* | 11/2010 | Kruizinga et al. | 359/359 |
| 2011/0223543 A1 | 9/2011 | Banine et al. | |
| 2011/0304916 A1* | 12/2011 | Ushigome | 359/576 |
| 2012/0140197 A1* | 6/2012 | Bakker | 355/67 |
| 2012/0235049 A1* | 9/2012 | Wang | 250/372 |
| 2013/0016362 A1* | 1/2013 | Gong et al. | 356/610 |

\* cited by examiner

Ray footprint at IF

| TDI-coated thin film | | |
|---|---|---|
| Be | | |
| K(13.5) | 1.7E-03 | |
| K(1030) | 4.0E+00 | |
| Thickness | 1.1E+02 nm | |
| T(13.5) | 8.4E-01 | |
| T(1030) | 4.2E-03 | |
| T(13.5)/T(1030) | 2.0E+02 | |
| | | |
| Zr | | |
| K(13.5) | 3.8E-03 | |
| K(1030) | 5.0E+00 | |
| Thickness | 9.2E+01 nm | |
| T(13.5) | 7.2E-01 | |
| T(1030) | 3.6E-03 | |
| T(13.5)/T(1030) | 2.0E+02 | |

PHASE GRATING FOR MASK INSPECTION SYSTEM

CROSS-REFERENCE TO RELATED APPLICATIONS

The present application claims the benefit under 35 U.S.C. §119(e) of U.S. Provisional Application Ser. No. 61/725,223, filed Nov. 12, 2012. Said U.S. Provisional Application Ser. No. 61/725,223 is hereby incorporated by reference in its entirety.

TECHNICAL FIELD

The disclosure generally relates to the field of mask inspection, and particularly to providing phase grating for mask inspection.

BACKGROUND

Mask inspection, or photo mask inspection, is an operation of checking the correctness of the fabricated photo masks (e.g., used for semiconductor device fabrications). Modern technologies for locating defects in photo masks are automated systems that involve scanning electron microscopy and other advanced tools. Existing optical systems in the market for mask inspection employ ultra-violet light at or above 193 nm that are not sufficient to resolve the features and defects below the 22 nm node. In order to resolve features and defects below 22 nm node, light of shorter wavelength in the EUV (e.g., 13.5 nm) region needs to be used.

Laser produced plasma (LPP) is a good candidate light source for extreme ultraviolet (EUV) mask inspection. LPP light source may use Xenon as fuel and Nd:YAG laser at wavelength near 1030 nm as driver laser. It has been observed that a few percent of the driver laser may enter the inspection system and cause enough detrimental thermal damage and image flare, and thus its intensity needs to be significantly reduced. Out of band radiation with wavelength from a few nm to 1000 nm also exists in the light source and needs to be suppressed.

While there are some Spectral Purity Filter (SPF) methods available, they are developed for EUV lithography which use CO2 laser of wavelength 10.6 um on Sn target. That is, these SPF methods are not developed specifically for mask inspection using Xenon LPP source with 1030 nm light, and due to the significant difference in laser wavelength (e.g., ten times the difference) and different use cases between inspection and lithography, the existing SPF methods are not applicable for EUV mask inspection.

Therein lies a need for providing phase grating for mask inspection without the aforementioned shortcomings.

SUMMARY

The present disclosure is directed to phase grating on a near normal incidence mirror. The mirror comprising a substrate; a plurality of continuous base bilayers positioned on the substrate; and a plurality of gratings positioned on the plurality of continuous base bilayers, wherein each of the plurality of gratings is formed using between 10 and 200 bilayers.

An additional embodiment of the present disclosure is directed to phase grating on a grazing incidence mirror. The mirror comprising a substrate; a continuous Ru base layer positioned on the substrate; and a plurality of Ru gratings positioned on the continuous Ru base layer, wherein a depth of the gratings is determined based on an angle of incidence.

A further embodiment of the present disclosure is directed to a mirror. The mirror comprising: a substrate, the substrate having a grated surface defining a plurality of gratings, wherein each of the plurality of gratings having a depth of approximately (laser wavelength)/4/cos(angle of incidence), a pitch of the gratings is a predetermined value between 5 and 1000 um, and a duty ratio of the gratings is a predetermined value between 0.7 and 1.5; and a coating layer deposited on the reflective substrate, the coating layer covering the entirety of the grated surface.

A further embodiment of the present disclosure is directed to a mask inspection system. The mask inspection system includes a laser configured for driving an EUV light source, a collector configured for collecting the EUV light and delivering the EUV light via an illumination module to an EUV mask, and a light sensor configured for receiving imaging of the EUV mask. The collector and the illumination module each include at least one mirror with phase grating. If the mirror is a normal incidence mirror, the phase grating includes a plurality of gratings formed using between 10 and 200 bilayers. Otherwise, if the mirror is a grazing incidence mirror, the phase grating includes a plurality of Ru gratings.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure is directed to Spectral Purity Filters, or SPFs, that are designed to block out the 1030 nm drive laser and other undesired out of band light in an EUV mask inspection system. Different phase grating designs for near normal incidence and grazing incidence are provided in the present disclosure and are configured specifically for EUV mask inspection.

Figure 1:
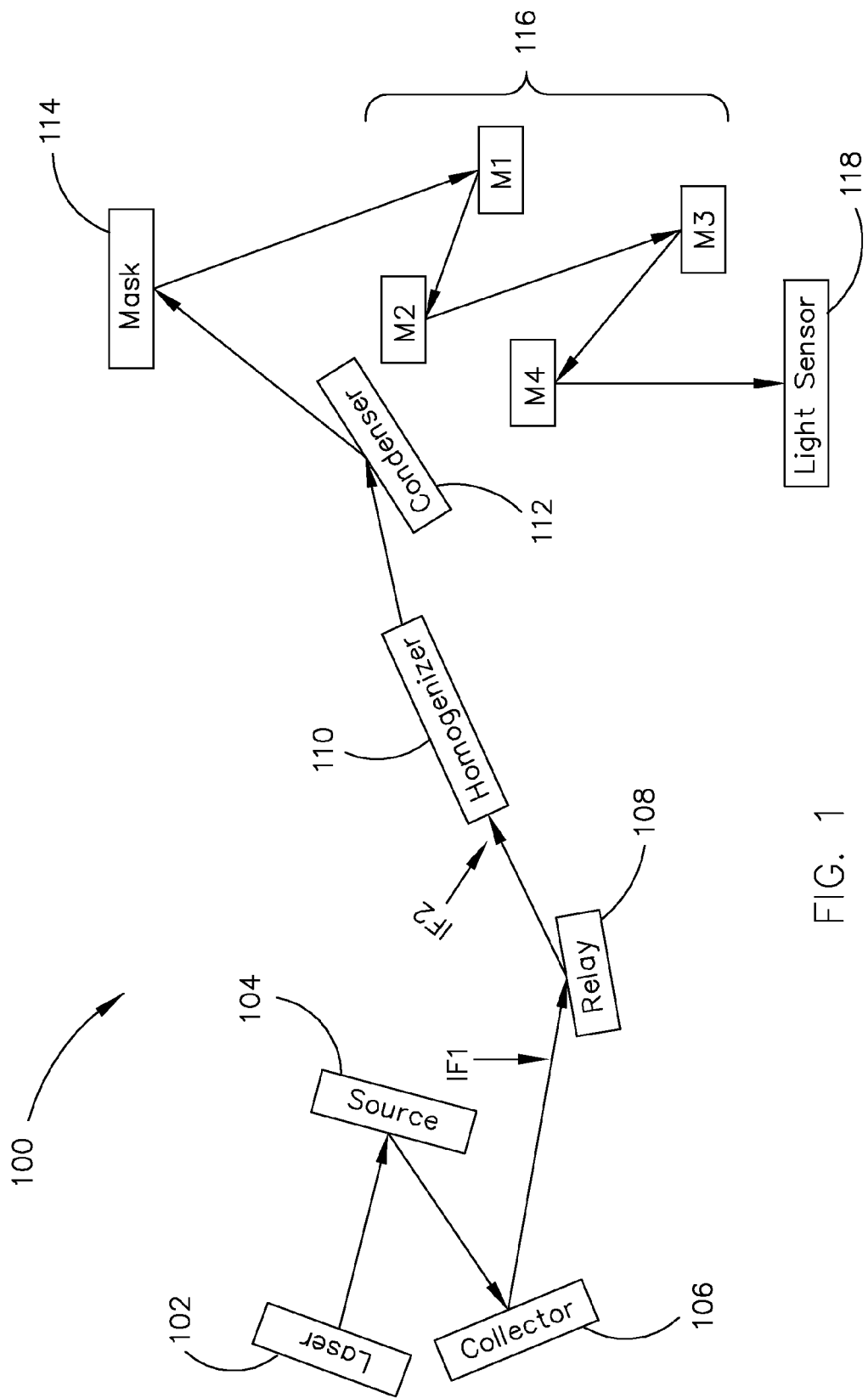
FIG. 1 is a block diagram depicting a mask inspection system.

Referring to FIG. 1, a block diagram depicting an exemplary EUV mask inspection system 100 is shown. In this example, the EUV light source 104 driven by a laser 102 is focused by a collector 106, delivered by an illumination module (comprising a relay mirror 108, a homogenizer 110 and one or more condenser mirrors 112) to an EUV mask 114, which is then imaged by an objective (comprising M1-M4) 116 to a light sensor 118.

In accordance with one embodiment of the present disclosure, requirements for SPF for the purpose of mask inspection are that the intensity of the 1030 nm light scattered from the source 104 to the objective 116 needs to be reduced by a factor of 50, and that the relative intensity of 1030 nm vs. 13.5 nm light from the source 104 to the light sensor 118 needs to be reduced by a factor of 2000. To comply with such requirements, different phase grating designs are provided and applied to various mirrors in the mask inspection system 100. In accordance with the present disclosure, the phase grating design for normal incidence mirrors is configured differently than the phase grating design for grazing incidence mirrors.

Referring generally to FIGS. 2 through 5, a phase grating design for normal incidence mirrors is shown. More specifically, the collector 106 depicted in FIG. 1 is shown here for illustrative purposes.

Figure 2:
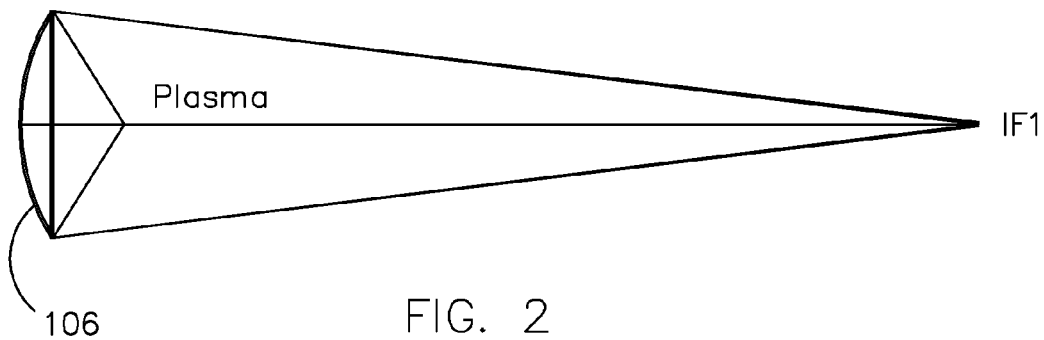
FIG. 2 is a side view depicting a normal incidence mirror.

As depicted in FIG. 2, the collector 106 is a part of an ellipsoid and is configured to focus light from the plasma source to an intermediate point labeled IF1. In accordance with the present disclosure, the collector 106 is a multilayer mirror that includes a substrate 402 and multiple base Mo/Si bilayers 404 positioned on top of the substrate 402. In one embodiment, the Mo/Si bilayer includes a Mo layer of thickness 2.5 to 3.5 nm and a Si layer of thickness 4 to 5 nm. In one embodiment, at least 35 base Mo/Si bilayers 404 are positioned on top of the substrate 402 to form the base of the collector 106. The substrate can be made of quartz, metal, glass, alloy and the like. It is contemplated that while FIG. 2 shows the collector 106 as symmetric to the optical axis, the collector can also be made of off-axis portion of an ellipsoid without departing from the spirit and scope of the present disclosure.

Figure 3:
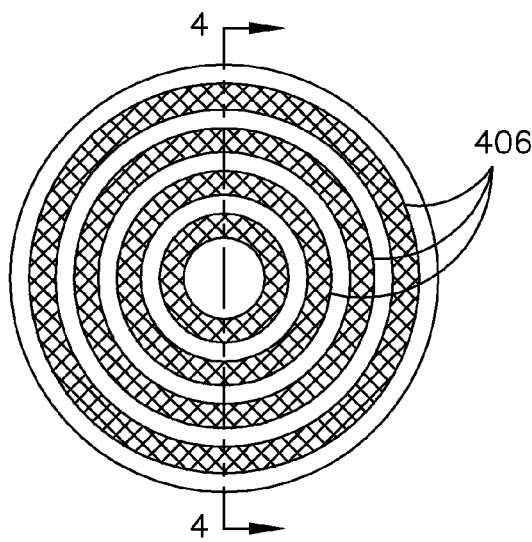
FIG. 3 is a front view of the normal incidence mirror having a plurality of radial gratings.
Figure 4:
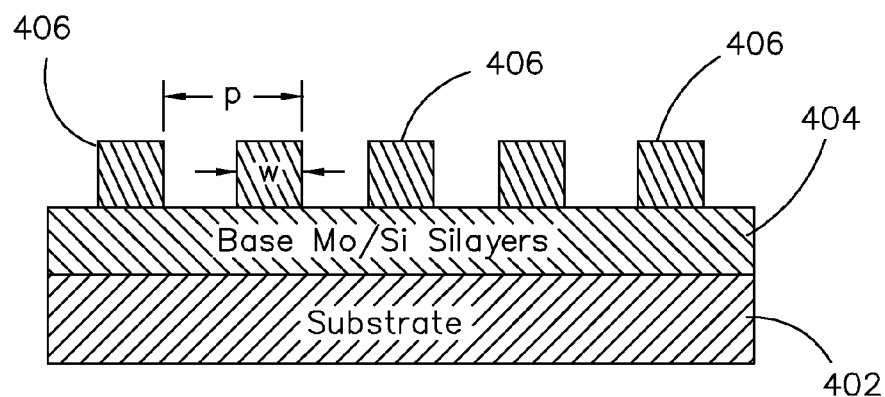
FIG. 4 is a cross-sectional view of the normal incidence mirror having a plurality of radial gratings.

As depicted in FIGS. 3 and 4, a plurality of radial gratings 406 are positioned on top of the base Mo/Si bilayers 404. Similar to the base Mo/Si bilayers 404, each one of the plurality of radial gratings 406 is also formed using multiple Mo/Si bilayers. While the number of Mo/Si bilayers may vary based on specific implementation, simulation results have indicated that each radial grating 406 should include between 10 and 200 Mo/Si bilayers. In one specific configuration where the wavelength of the driver laser is 1030 nm, each radial grating 406 includes between 33 and 43 Mo/Si bilayers.

It is contemplated that additional protective coating may be applied to the gratings 406. For instance, a coating (e.g., approximately 2 nm thick) containing Ru, C, Pt, Pd, Au, Nb, Nb2O5, SiO2, TiO2, or RuO2 may be deposited on the top and/or the base (where it contacts the base 404) of each grating 406. It is understood, however, that such protective coatings are optional and the particular material used for the coating may vary without departing from the spirit and scope of the present disclosure.

It is also contemplated that the gratings 406 are arranged in certain manners in order to optimize the performance. More specifically, the pitch (indicated as P in FIG. 4) of the grating is a predetermined value between 5 and 1000 um, and preferably between 10 and 200 um. In addition, the duty ratio (i.e., $$\frac{w}{p-w}$$

as indicated in FIG. 4) of the grating is also a predetermined value between 0.7 and 1.5, and preferably between 0.9 and 1.1. As previously mentioned, the arrangement of the gratings described above is optimized for mirrors having near normal incidences.

Figure 5:
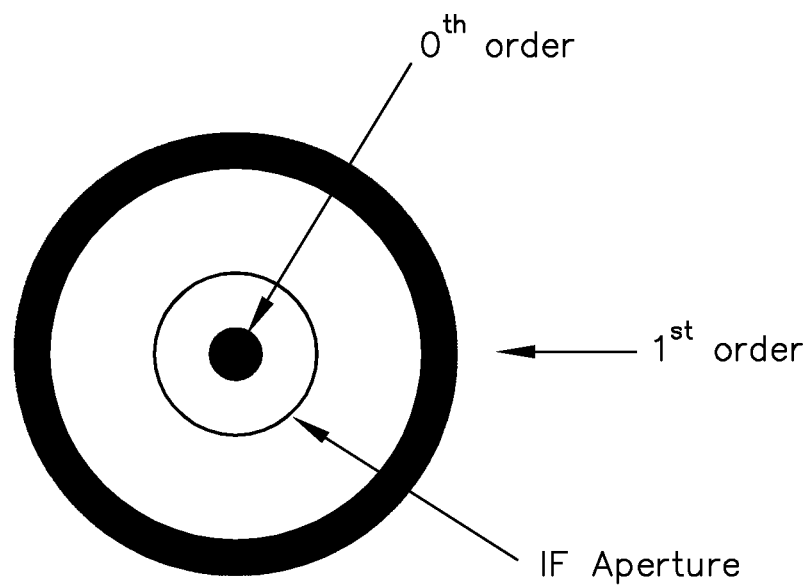
FIG. 5 is an illustration depicting the ray footprint at IF1 of the mask inspection system of FIG. 1.

FIG. 5 is an illustration depicting the ray footprint at IF1 of the mask inspection system 100. It is noted that the $1^{st}$ and higher orders of the undesired 1030 nm are diffracted and blocked by an aperture at the IF1, which only allows the EUV and the $0^{th}$ order of 1030 nm to enter the illumination module. In accordance with the present disclosure, the $0^{th}$ order of the 1030 nm light is greatly suppressed by the phase grating design implemented on the collector 106. On the other hand, the wavelength in the EUV (e.g., 13.5 nm) region has good reflection from both the base and the top surfaces, therefore providing desirable SPF for the illumination module downstream.

Figure 6:
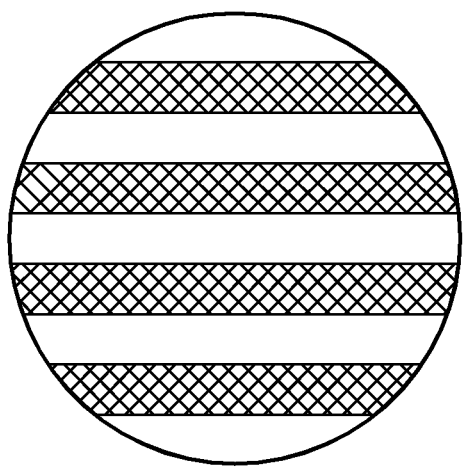
FIG. 6 is a front view of a normal incidence mirror having a plurality of parallel gratings.

It is contemplated that the gratings 406 describe above are not required to be arranged in a radial/circular pattern. The grating grooves may also form parallel line pattern as shown in FIG. 6, as well as other patterns (e.g., in a off-axis radial manner, a combination of different parallel sections, or a combination of different radial sections) without departing from the spirit and scope of the present disclosure.

Figure 7:
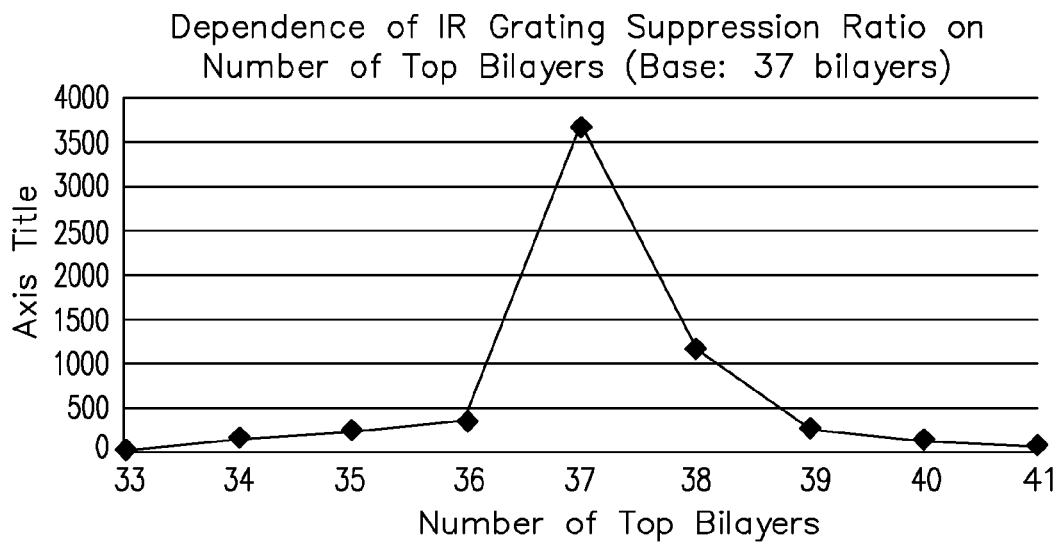
FIG. 7 is a chart illustrating dependence of grating IR (1030 nm) suppression factor on the number of top bilayers, where the number of base bilayers is 37, the pitch is 20 um, the duty ratio is 1, the plane of incidence is parallel to the groove, the angle of incidence is 0° and the period of Mo/Si bilayer is 6.96 nm.

As previously mentioned, simulation results have indicated that each radial grating 406 should include between 10 and 200 Mo/Si bilayers, and preferably between 33 and 43 Mo/Si bilayers for 1030 nm light. FIG. 7 shows the dependence of the grating suppression factor on the number of top bilayers. The grating suppression factor is defined as the ratio of the reflectivity of a blank Mo/Si multilayer to 1030 nm light and the $0^{th}$ order reflectivity of the phase grating to 1030 nm light. As can be seen, the infrared (IR at 1030 nm) suppression ratio is the largest for the number of top bilayers to be 37. The number of top bilayers also defines the depth of the gratings. The phase shift caused by such depth between reflected IR light from the top bilayers and from the base bilayers is, in the case of normal incidence, $$\frac{37 \times 6.96 \times 2}{1030 \times 2\pi} = \pi,$$

which causes destructive interference and thus minimizes the $0^{th}$ order diffraction.

Figure 8:
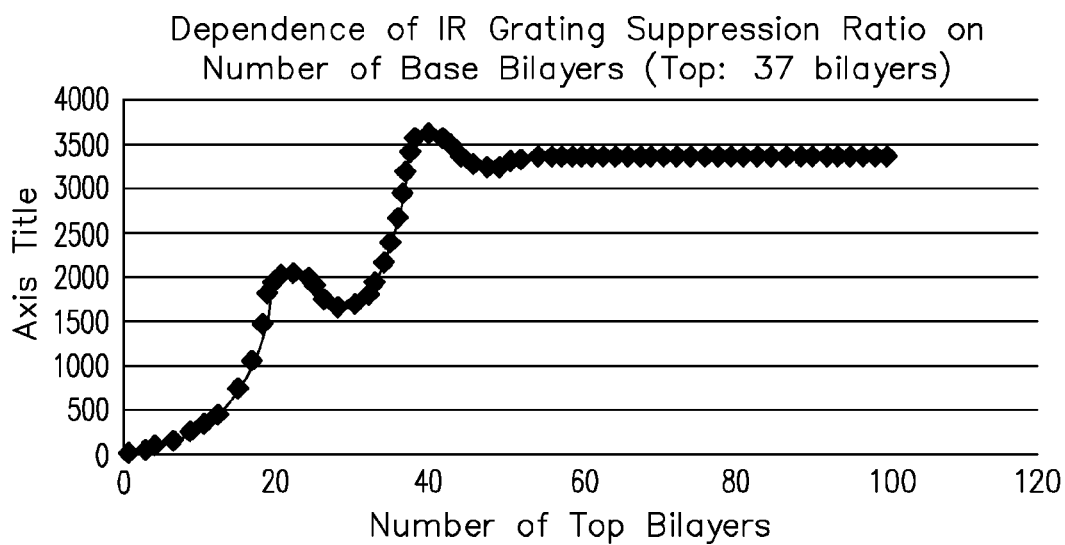
FIG. 8 is a chart illustrating dependence of grating IR (1030 nm) suppression factor on the number of base bilayers, where the number of base bilayers is 37, the pitch is 20 um, the duty ratio is 1, the plane of incidence is parallel to the groove, the angle of incidence is 0° and the period of Mo/Si bilayer is 6.96 nm.

Similarly, simulation results have indicated that the base 404 should include at least 35 base Mo/Si bilayers for 1030 nm light. FIG. 8 shows the dependence of the grating suppression factor on the number of base bilayers. As can be seen, for high IR suppression ratio, the number of base bilayers needs to be at least 35 to achieve high reflectivity of EUV light.

It is contemplated that the same grating design described above can be applied on graded multilayer to achieve high IR suppression ratio for angle of incidence ranging between 0 and 30 degrees. In one embodiment, the graded multilayer is designed so that the multilayer period varies based on the angle of incidence and follows approximately: multilayer period=13.5 nm/2/cos(angle of incidence). Such graded multilayer designs are used to increase the overall reflectivity of the mirror to EUV light. In addition, to achieve high IR suppression factor, the depth of the phase grating also needs to vary with the angle of incidence following approximately: grating depth=(laser wavelength)/4/cos(angle of incidence), or in the range of 100-600 nm. In accordance with this design, since the grating depth is equal to the number of top bilayers multiplied by the multilayer period, the number of top bilayers can be kept the same across the entire mirror (collector in the example above) for a given angle of incidence range between 0 and 30 degrees. Simulation results also indicated that the number of base bilayers and the duty ratio can be the same to achieve high IR suppression ratio. Keeping the same grating structure across the entire mirror/collector greatly simplifies its manufacturing process and may be appreciated in various applications.

It is further contemplated that while the Mo/Si bilayers are referenced in the description above, bilayers including other alternative materials may also be utilized without departing from the spirit and scope of the present disclosure. For instance, any high reflective multilayer structure for EUV may be utilized, including, but not limited to, Ru/Si, Ru/C, Mo/C, Mo/C, Si/C, La/B, La/B4C, Ru/B4C, Ti/B4C, LaN/B4C or LaN/B bilayers.

Figure 9:
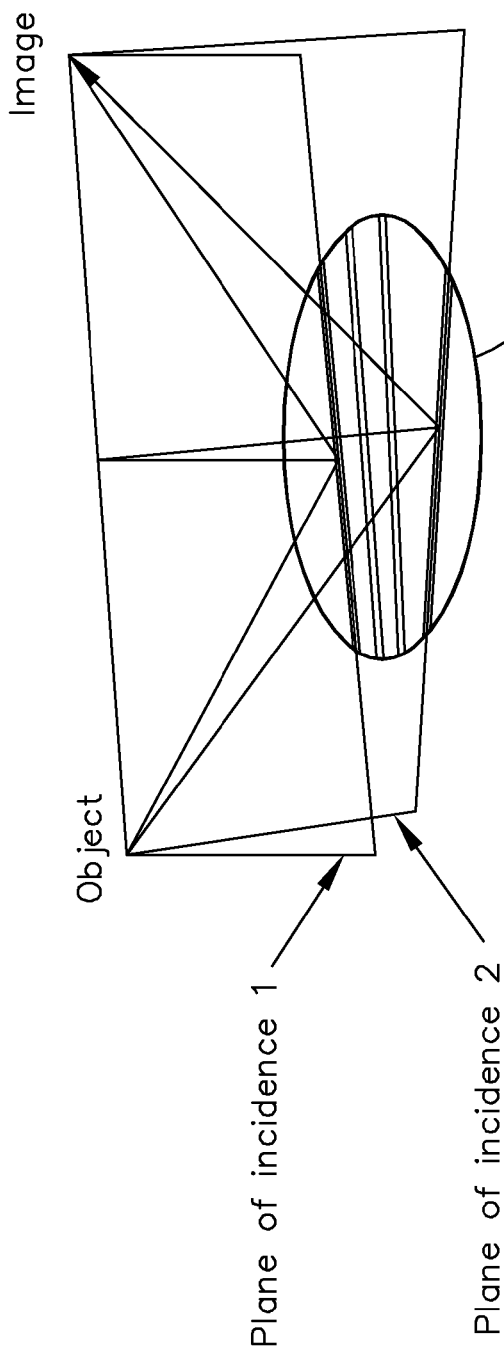
FIG. 9 is an illustration depicting a grazing incidence mirror having a plurality of gratings.
Figure 10:
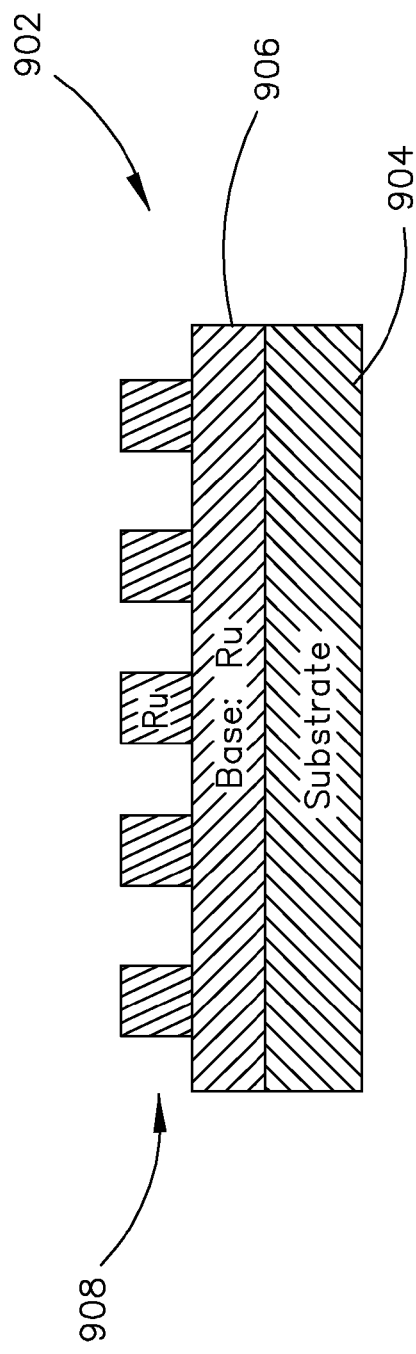
FIG. 10 is a cross-sectional view of the grazing incidence mirror of FIG. 9.

Referring generally now to FIGS. 9 and 10, a phase grating design for grazing incidence mirrors is shown. More specifically, such a phase grating design is applicable to the relay mirror 108 or the condenser mirrors 112 in the example depicted in FIG. 1.

As depicted in FIG. 9, the mirror 902 can be a focusing mirror to relay one source image to another image. The mirror substrate 904 may include materials such as glass, silicon, as well as metals that are of good thermal transport efficiency and easy to polish to get very low surface roughness. On top of the substrate 904 is a base layer of coating 906 (such as Ru) with a thickness of at least 50 nm. On top of the base layer of coating 906 is a top layer 908 of the same material as 906 that is etched to form grating grooves.

It is contemplated that the top layer 908 is arranged in certain manners in order to optimize the performance. More specifically, the grating grooves are preferably kept parallel to the planes of incidence as illustrated in FIG. 9. The thickness of the top layer 908 is approximately (laser wavelength)/4/cos(angle of incidence), and the duty ratio (bottom/top width) of the grating ranges between 0.7-1.5. In addition, the pitch of the grating ranges between 5 and 1000 um, and preferably between 10 and 200 um. Furthermore, the typical range of angle of incidence to the mirror 902 is 66 to 86 degrees. Simulation results have indicated that such arrangements greatly suppress the $0^{th}$ order of the 1030 nm light at grazing incidence.

Simulation results have indicated that the phase grating design illustrated in FIGS. 9 and 10 is effective for different angles of incidence. As mentioned previously, for small pitches, the grating depth and duty ratio can be varied to achieve maximum IR suppression ratio. For the example of grating of 20 um pitch, the groove depth needs to be changed away from the depth that will cause half a wavelength shift (i.e., wavelength/4/cos(angle of incidence), or in the range of 300-5000 nm), and the duty ratio needs to change between 1 and 1.3 to achieve optimum IR suppression ratio. With such optimization, the IR suppression ratio can achieve above 100 in the typical range of angle of incidence from 66 to 86 degrees.

It is also contemplated that for both near normal and grazing incidence mirrors, the pitch of the grating is often limited by the distance between the mirror and the intermediate focus (IF1 or IF2). For example, if the distance between the mirror and the intermediate focus, l, is 200 mm, and the distance between the $0^{th}$ and $1^{st}$ order intermediate focus, a, is 10 mm, the pitch needs to be small enough to separate the $0^{th}$ order from the $1^{st}$ order. More specifically, in one embodiment, the grating pitch value is determined based on $$d < l \times \frac{\text{wavelength}}{a} \leq 20\ um.$$

In the example above, the pitch is determined to be approximately 20 um.

Figure 11:
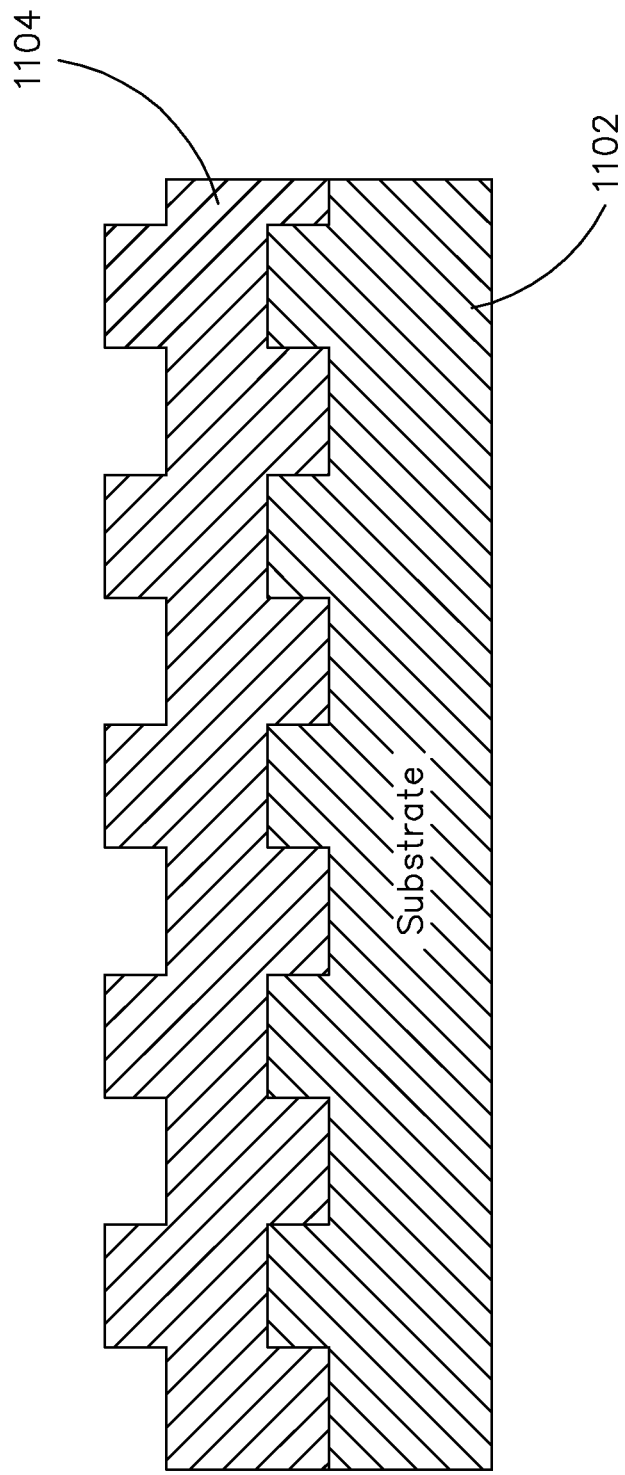
FIG. 11 is a cross-sectional view of a coating deposited on a grated substrate.

Now, it is noted that the phase grating designs illustrated in FIGS. 2 through 6 as well as FIGS. 9 and 10 both describe gratings on coated substrates. It is contemplated that an alternative approach is to provide coatings on grated substrates, as illustrated in FIG. 11. As depicted in FIG. 11, the substrate 1102 is a grated substrate, and a layer of coating 1104 is applied on top of the grated substrate 1102.

It is contemplated that the configuration depicted in FIG. 11 can be utilized to provide phase grating for both normal incidence and/or grazing incidence mirrors. For instance, for a normal incidence mirror, the substrate protrusion may follow the same thickness as the grating depth (laser wavelength)/4/cos(angle of incidence). The multilayer thickness is the same in the top and the groove for a fixed angle of incidence. The coating layer 1104 may include the same type of Mo/Si bilayers, and the number of such bilayers need to be at least 35, and can be as high as 100-200. Other parameters, including pitch, duty ratio, coating, bilayer thickness as function of angle of incidence and the like may be configured in the same manner as the normal incidence mirrors described above.

Similarly, the configuration depicted in FIG. 11 can be utilized to provide phase grating for grazing incidence mirrors as well. For instance, the substrate protrusion may follow the same thickness as the grating depth (laser wavelength)/4/cos(angle of incidence). The thickness of the coating layer (e.g., Ru) 1104 may be the same in the top and the groove for a fixed angle of incidence. Other parameters, including pitch, duty ratio, coating thickness as function of angle of incidence and the like may be configured in the same manner as the grazing incidence mirrors described above.

Figures 12, 13:
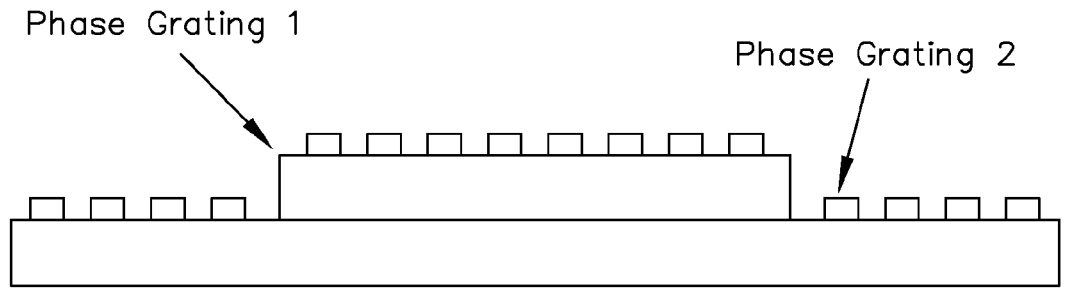
FIG. 12 is a cross-sectional view of a mirror having more than one type of phase gratings.
FIG. 13 shows examples of thin film Be and Zr coatings on light sensor to achieve the transmission ratio (13.5 nm/1030 nm) of 200.

Referring now to FIG. 12, a hybrid phase grating design is depicted. The hybrid phase grating design provides more than one type of grating to suppress multiple wavelengths. For instance, the grating can have two (or more) different components, one with large pitch and deep depth to suppress a long wavelength, and the other with smaller pitch and shallower depth to suppress a shorter wavelength. It is contemplated that both grating components may incorporate the phase grating design for normal incidence mirrors as described in FIGS. 2 through 5, or they may both incorporate the phase grating design for grazing incidence mirrors as described in FIGS. 9 and 10. In certain instances, one of the two (or more) different components may incorporate the phase grating design for normal incidence mirrors and the other may incorporate the phase grating design for grazing incidence mirrors. Various combinations of different phase grating designs may be implemented without departing from the spirit and scope of the present disclosure.

In addition to phase grating designs described above, coating may be applied to the light sensor 118 (e.g., a TDI sensor) to further improve the performance of EUV mask inspection. FIG. 13 shows typical thickness of Be and Zr coating on the light sensor 118. Be and Zr are found to be most efficient in blocking 1030 nm light while absorbing few amount of EUV light. For example, if applying coating of thin film on the light sensor 118 with target of 200 times relative laser/EUV intensity suppression, then the thickness of Be needs to be ~113 nm, the thickness of Zr needs to be ~92 nm, and the EUV loss is 16% with Be or 27% with Zr.

It is contemplated that all three or any two of the spectral purity filtering methods described above (i.e., grating on normal incidence mirrors, grating on grazing incidence mirrors, and thin film coating on light sensor) can be combined to satisfy SPF requirements with minimum EUV lost.

It is also contemplated that in addition to 1030 nm laser referenced above, all lasers in the wavelength range from 500 to 2000 nm can be used as the pump laser for Xenon EUV source with high enough laser-to-EUV conversion efficiency. The grating designs described above can be tuned accordingly to suppress such pump lasers. Furthermore, the grating designs described above may also be applied on other mirrors in the illuminator (for example, homogenizer and condenser) to further suppress pump laser. They may also be applied to such mirror to suppress DUV radiation in the wavelength range ~130 to ~400 nm.

Figure 14:
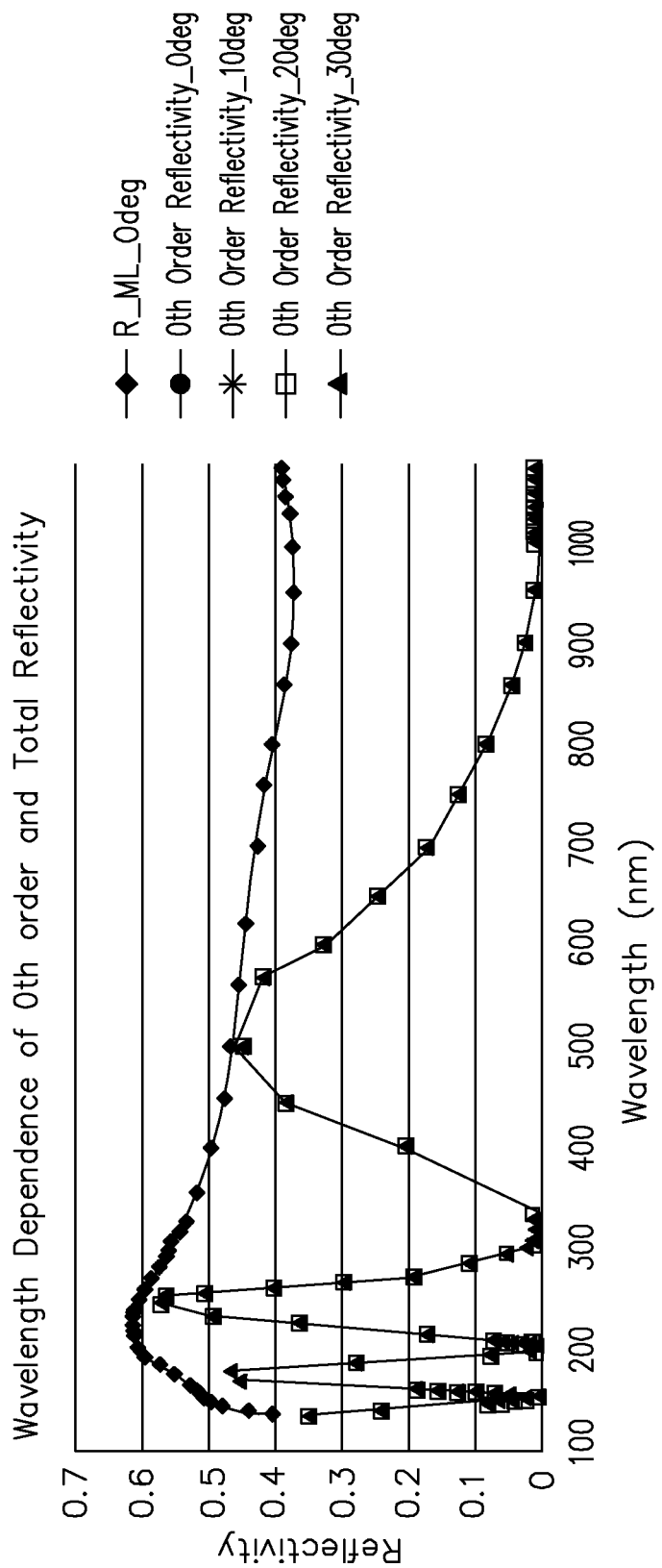
FIG. 14 is a chart illustrating suppression of reflectivity in the wavelength range ~130 to ~400 nm.
Figure 15:
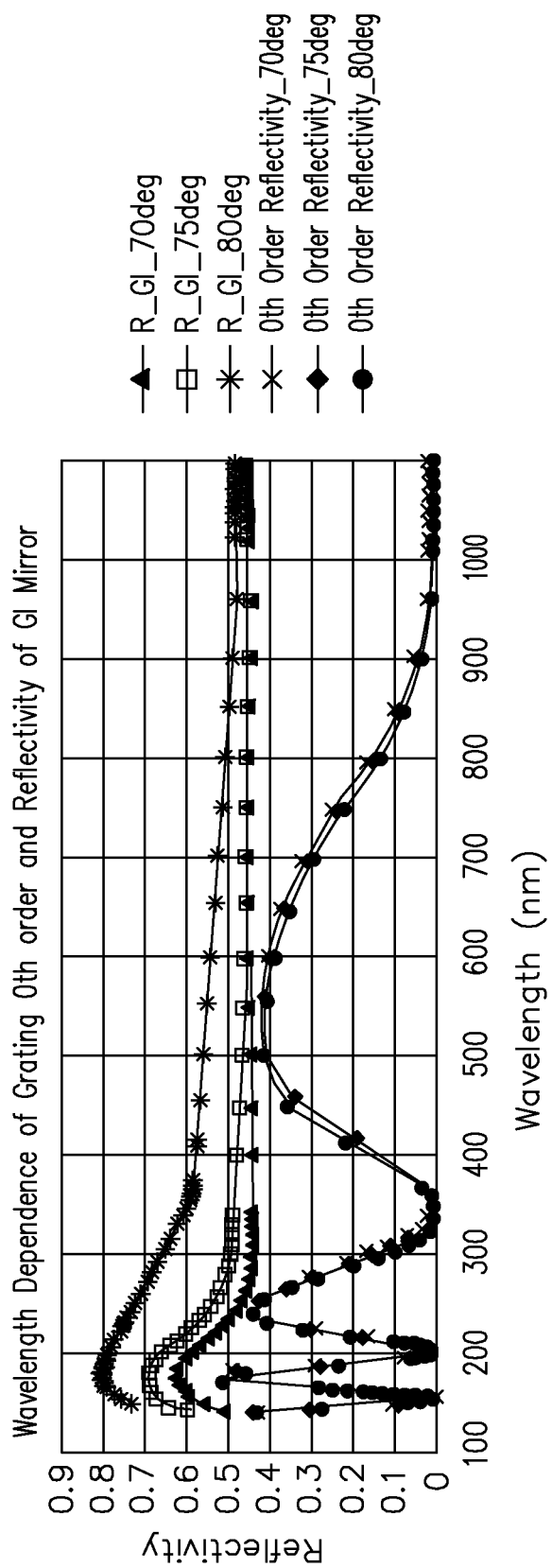
FIG. 15 is another chart illustrating suppression of reflectivity in the wavelength range ~130 to ~400 nm.

FIG. 14 shows the calculated $0^{th}$ order reflectivity from 130 to 1050 nm when the phase grating design for normal incidence mirrors described above is used. The particular grating structure utilized for this simulation includes 37 top bilayers, 37 base bilayers, angle of incidence between 0-30 degrees, grating period=6.9/cos(angle of incidence), pitch=30*wavelength and duty ratio=1. FIG. 15 shows the calculated $0^{th}$ order reflectivity from 130 to 1050 nm when the phase grating design for grazing incidence mirrors described above is used. The particular grating structure utilized for this simulation includes a Ru coating having a thickness of about 5 um, grating depth=1030/4/cos(angle of incidence), pitch=30*wavelength and duty ratio=1.05 with plane of incidence parallel to the groove.

As shown in FIGS. 14 and 15, the phase grating configurations not only provide suppression in the wavelength around 1030 nm, but also provide suppression in the wavelength range ~130 to ~400 nm. Furthermore, it is contemplated that the specific parameters used in the calculations above may be modified without departing from the spirit and scope of the present disclosure.

It is further contemplated that the EUV mask inspection system depicted in FIG. 1 is merely exemplary. The spectral purity filtering methods described in the present disclosure are applicable to EUV mask inspection systems that may differ from the system depicted in FIG. 1 without departing from the spirit and scope of the present disclosure.

The methods disclosed may be implemented as sets of instructions, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A phase grating on a mirror, comprising:
a substrate;
a plurality of continuous base bilayers positioned on the substrate; and
a plurality of gratings positioned on the plurality of continuous base bilayers, wherein a depth of the plurality of gratings is approximately (laser wavelength)/4/cos (angle of incidence).

2. The phase grating of claim 1, wherein the continuous base bilayers and the plurality of gratings are formed using at least one of: Mo/Si bilayers, Ru/Si bilayers, Ru/C bilayers, Mo/C bilayers, Mo/C bilayers, Si/C bilayers, La/B bilayers, La/B4C bilayers, Ru/B4C bilayers, Ti/B4C bilayers, LaN/B4C bilayers or LaN/B bilayers.

3. The phase grating of claim 1, wherein each of the plurality of gratings is formed using between 10 and 200 bilayers.

4. The phase grating of claim 1, wherein the gratings are arranged in at least one of: a parallel manner, a radial manner, an off-axis radial manner, a combination of different parallel sections, a combination of different radial sections, or a combination of parallel and radial sections.

5. The phase grating of claim 1, wherein a pitch of the plurality of gratings is a predetermined value between 5 and 1000 um.

6. The phase grating of claim 1, wherein a duty ratio of the gratings is a predetermined value between 0.7 and 1.5.

7. The phase grating of claim 1, wherein the depth of the gratings is between 100 and 600 nm.

8. The phase grating of claim 1, further comprising:
a coating containing at least one of: Ru, C, Pt, Pd, Au, Nb, Nb2O5, SiO2, TiO2 or RuO2 deposited on each of the plurality of gratings.

9. A phase grating on a mirror, comprising:
a substrate;
a continuous Ru base layer positioned on the substrate, the continuous Ru base layer having a thickness of at least approximately 50 nm; and
a plurality of Ru gratings positioned on the continuous Ru base layer, wherein a depth of the gratings is determined based on an angle of incidence.

10. The phase grating of claim 9, wherein the Ru gratings are arranged to be approximately parallel to planes of incidence.

11. The phase grating of claim 9, wherein a pitch of the gratings is between 5 and 1000 um.

12. The phase grating of claim 9, wherein a duty ratio of the gratings is between 0.7 and 1.5.

13. The phase grating of claim 9, wherein the depth of the gratings is between 300 and 5000 nm.

14. A mirror, comprising:
a substrate, the substrate having a grated surface defining a plurality of gratings, wherein each of the plurality of gratings having a depth of approximately (laser wavelength)/4/cos(angle of incidence), a pitch of the gratings is a predetermined value between 5 and 1000 um, and a duty ratio of the gratings is a predetermined value between 0.7 and 1.5; and
a coating layer deposited on the reflective substrate, the coating layer covering the entirety of the grated surface.

15. The mirror of claim 14, wherein the laser wavelength is in a range between 500 and 2000 nm.

16. The mirror of claim 14, wherein the angle of incidence is between 0 and 30 degrees.

17. The mirror of claim 16, wherein the coating layer is formed using between 10 and 200 bilayers formed using at least one of: Mo/Si bilayers, Ru/Si bilayers, Ru/C bilayers, Mo/C bilayers, Mo/C bilayers, Si/C bilayers, La/B bilayers, La/B4C bilayers, Ru/B4C bilayers, Ti/B4C bilayers, LaN/B4C bilayers or LaN/B bilayers.

18. The mirror of claim 16, wherein the gratings are arranged in at least one of: a parallel manner, a radial manner, an off-axis radial manner, a combination of different parallel sections, a combination of different radial sections, or a combination of parallel and radial sections.

19. The mirror of claim 14, wherein the angle of incidence is between 66 and 86 degrees.

20. The mirror of claim 19, wherein the coating layer is formed using Ru.

21. The mirror of claim 19, wherein the gratings are arranged to be parallel to planes of incidence.

22. A mask inspection system, comprising:
a laser configured for driving an EUV light source;
a collector configured for collecting the EUV light and delivering the EUV light via an illumination module to an EUV mask;
a light sensor configured for receiving imaging of the EUV mask;
wherein the collector and the illumination module each includes at least one mirror, said at least one mirror having phase grating to suppress undesired radiations;
wherein if an angle of incidence to said at least one mirror is between 0 and 30 degrees, said phase grating includes a plurality of gratings each having a depth of approximately (laser wavelength)/4/cos(angle of incidence).

23. The mask inspection system of claim 22, wherein each of the plurality of gratings is formed using at least one of: Mo/Si bilayers, Ru/Si bilayers, Ru/C bilayers, Mo/C bilayers, Mo/C bilayers, Si/C bilayers, La/B bilayers, La/B4C bilayers, Ru/B4C bilayers, Ti/B4C bilayers, LaN/B4C bilayers or LaN/B bilayers.

24. The mask inspection system of claim 22, wherein the laser is in a wavelength range between 500 and 2000 nm.

25. The mask inspection system of claim 22, wherein if the angle of incidence to said at least one mirror is between 0 and 30 degrees, the gratings are arranged in at least one of: a parallel manner, a radial manner, an off-axis radial manner, a combination of different parallel sections, a combination of different radial sections, or a combination of parallel and radial sections.

26. The mask inspection system of claim 22, wherein if the angle of incidence to said at least one mirror is between 66 and 86 degrees, said phase grating includes a plurality of Ru gratings arranged to be parallel to planes of incidence.

27. The mask inspection system of claim 22, wherein a pitch of the gratings is a predetermined value between 5 and 1000 um, and a duty ratio of the gratings is a predetermined value between 0.7 and 1.5.

28. The mask inspection system of claim 22, wherein the phase grating is configured to simultaneously suppress laser and UV light.

29. The mask inspection system of claim 22, wherein said at least one mirror is further configured to have at least two types of phase gratings.

30. The mask inspection system of claim 22, wherein the light sensor is coated with a thin film coating.

31. The mask inspection system of claim 30, wherein the thin film coating on the light sensor includes at least one of: Be and Zr.

32. A phase grating on a mirror, comprising:
a substrate;
a plurality of continuous base bilayers positioned on the substrate; and
a plurality of gratings positioned on the plurality of continuous base bilayers, wherein each of the plurality of gratings is formed using a number of bilayers, wherein a depth of the plurality of gratings is approximately (laser wavelength)/4/cos(angle of incidence).

33. The phase grating of claim 32, wherein each of the number of gratings includes between 10 and 200 bilayers, and wherein the continuous base bilayers and the plurality of gratings are formed using at least one of: Mo/Si bilayers, Ru/Si bilayers, Ru/C bilayers, Mo/C bilayers, Mo/C bilayers, Si/C bilayers, La/B bilayers, La/B4C bilayers, Ru/B4C bilayers, Ti/B4C bilayers, LaN/B4C bilayers or LaN/B bilayers.

34. The phase grating of claim 32, wherein a pitch of the gratings is a predetermined value between 5 and 1000 um.

35. The phase grating of claim 32, wherein a duty ratio of the gratings is a predetermined value between 0.7 and 1.5.

36. The phase grating of claim 32, wherein the laser wavelength is in a range between 500 and 2000 nm.

37. The phase grating of claim 32, further comprising:
a coating containing at least one of: Ru, C, Pt, Pd, Au, Nb, Nb2O5, SiO2, TiO2 or RuO2 deposited on each of the number of gratings.

* * * * *